US012746314B2

(12) United States Patent
Jansson et al.

(10) Patent No.: US 12,746,314 B2

(45) Date of Patent: Sep. 29, 2026

(54) AUTOMATED PERITONEAL DIALYSIS CYCLER HAVING GRAVIMETRIC CONTROL

(71) Applicants: BAXTER INTERNATIONAL INC., Deerfield, IL (US); BAXTER HEALTHCARE SA, Glattpark (CH)

(72) Inventors: Olof Jansson, Vellinge (SE); Christian Antero Vartia, Veberod (SE); Sture Hobro, Lund (SE)

(73) Assignees: Vantive US Healthcare LLC, Deerfield, IL (US); Vantive Health GmbH, Glattpark (CH)

( * ) Notice: Subject to any disclaimer, the term of this patent is extended or adjusted under 35 U.S.C. 154(b) by 469 days.

(21) Appl. No.: 18/278,711

(22) PCT Filed: Feb. 24, 2022

(86) PCT No.: PCT/US2022/017749

§ 371 (c)(1),
(2) Date: Aug. 24, 2023

(87) PCT Pub. No.: WO2022/192000

PCT Pub. Date: Sep. 15, 2022

(65) Prior Publication Data

US 2024/0382660 A1 Nov. 21, 2024

Related U.S. Application Data

(60) Provisional application No. 63/153,085, filed on Feb. 24, 2021.

(51) Int. Cl.

*A61M 1/28* (2006.01)
*A61M 1/16* (2006.01)

(52) U.S. Cl.

CPC ............ *A61M 1/281* (2014.02); *A61M 1/166* (2014.02); *A61M 1/28* (2013.01); *A61M 1/282* (2014.02);

(Continued)

(58) Field of Classification Search

CPC ........ A61M 1/166; A61M 1/28; A61M 1/281; A61M 1/282; A61M 2202/0007;

(Continued)

(56) References Cited

U.S. PATENT DOCUMENTS 7,559,913 B1 7/2009 Jeppsson et al.

FOREIGN PATENT DOCUMENTS

| | | |
|---|---|---|
| CN | 103 394 141 | 4/1997 |
| JP | H09 108340 | 4/1997 |

(Continued)

OTHER PUBLICATIONS

English translation Chinese Patent Publication No. CN 103394141 A (2013).*

(Continued)

*Primary Examiner* — John Kim

(74) *Attorney, Agent, or Firm* — K&L Gates LLP

(57) ABSTRACT

A peritoneal dialysis ("PD") system includes a cycler having a weigh scale, a chamber for weighing by the weigh scale, a heater, a plurality of valves, a pump, and a control unit operable with the weigh scale, the heater, the plurality of valves and the pump; and a disposable set including a PD fluid container fitting within the chamber for weighing and heating, a supply line in fluid communication with the PD fluid container, a drain container fitting within the chamber for weighing, a drain line in fluid communication with the drain container, and a patient line positioned on an opposing side of the pump from the supply line and the drain lines, wherein the control unit is configured to operate the plurality (Continued)

of valves and the pump to pump used dialysis fluid to the drain container and fresh dialysis fluid from the PD fluid container.

26 Claims, 9 Drawing Sheets

(52) U.S. Cl.
CPC ............... *A61M 2202/0007* (2013.01); *A61M 2202/0014* (2013.01); *A61M 2202/04* (2013.01); *A61M 2205/106* (2013.01); *A61M 2205/123* (2013.01); *A61M 2205/3327* (2013.01); *A61M 2205/3393* (2013.01); *A61M 2205/36* (2013.01); *A61M 2205/3653* (2013.01); *A61M 2205/50* (2013.01)

(58) Field of Classification Search
CPC ...... A61M 2202/0014; A61M 2202/04; A61M 2205/106; A61M 2205/123; A61M 2205/3327; A61M 2205/3393; A61M 2205/36; A61M 2205/3653; A61M 2205/50
See application file for complete search history.

(56) References Cited

FOREIGN PATENT DOCUMENTS

| | | |
|---|---|---|
| WO | 2011079083 | 6/2011 |
| WO | 2022140054 | 6/2022 |

OTHER PUBLICATIONS

English translation Japanese Patent Publication No. JP 09-108340 A (1997).*
International Search Report, PCT/US2022/017749 dated Oct. 11, 2022—4 pages.
Written Opinion, PCT/US2022/017749 dated Oct. 11, 2022—22 pages.
IPRP PCT/US2022/017749 dated Apr. 12, 2023—24 pages.

* cited by examiner

AUTOMATED PERITONEAL DIALYSIS CYCLER HAVING GRAVIMETRIC CONTROL

PRIORITY CLAIM

The present application is a national phase entry of PCT Patent Application No. PCT/US2022/017749, filed on Feb. 24, 2022, which claims priority to and the benefit of U.S. Provisional Patent Application No. 63/153,085, filed on Feb. 24, 2021, the entirety of which are herein incorporated by reference.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal chamber, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending upon the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

There is also a need for APD devices to be portable so that a patient may bring his or her device on vacation or for work travel.

For each of the above reasons, it is desirable to provide a relatively simple, compact APD machine, which operates a simple and cost effective disposable set.

SUMMARY

The present disclosure relates to an automated peritoneal dialysis ("APD") machine or cycler, which provides a chamber sized to hold all of the fresh and used peritoneal dialysis ("PD") fluid, albeit at different times, used over the course of a treatment. A weigh scale may be positioned to weigh the chamber and any of the fresh of used PD fluid provided initially, any fresh PD fluid that enters during treatment, and any used PD fluid that leaves during treatment. In this manner, the weigh scale is able to monitor over an entire treatment, including an initial patient drain if needed, and output weight signals to a control unit so that fill and drain volumes may be monitored and known and an overall amount of patient ultrafiltration ("UF") at the end of treatment may be determined.

The chamber is also provided with a fluid heater, such as an electrical plate heater, which heats the fresh PD fluid provided in each PD fluid container or bag loaded into the chamber. The PD fluid containers or bags may be loaded on top of each other or side-by-side within the chamber as needed for proper heating. The PD fluid containers or bags may hold multiple patient fill volume's worth of fluid and a last fill container of icodextrin may be provided. The PD fluid containers or bags may hold different formulations, so that different patient fills may contain different dextrose or glucose levels. The different formulations may also be mixed for a single patient fill to provide a PD formulation optimized for the patient.

The PD fluid containers are connected to and fluidly communicate with an initially dry portion of the disposable set, which includes a common line connecting to each of the PD fluid container supply lines, a pumping (e.g., peristaltic pumping) line, a patient line and in one embodiment a terminal or final drain line. The disposable set may also include a drain container located within the chamber, which enables used dialysis fluid to be removed from the patient, delivered temporarily to the drain container for weighing, and then removed from the drain container to a house drain or final or terminal drain container, which may be performed during a patient dwell.

In an embodiment, the supply lines of the dry portion of the disposable set connect to container lines extending from fresh PD fluid supply containers. The connections may be made along a side, surface or wall of the chamber. In another embodiment, the supply lines of the dry portion of the disposable set extend through holes or slots in the side, surface or wall of the chamber for direct connection to the fresh PD fluid supply containers.

In another embodiment, a separate drain container is not provided and instead the PD fluid containers or bags accept used dialysis fluid or effluent from the patient. The PD fluid containers or bags may be partitioned by an interior polymer layer into separate fresh and used fluid compartments. Here, a supply line is placed in fluid communication with the fresh PD fluid compartment, while a drain line is placed in fluid communication with the used PD fluid compartment. Fresh dialysis fluid is delivered from the fresh PD fluid compartment, through the supply line, through the patient line, to the patient. Used dialysis fluid is delivered from the patient, through the patient line, through the drain line, to the drain compartment. In a variation of this embodiment, ports from the fresh PD fluid compartment and the used PD fluid compartment are each fitted with a one-way valve and are tee'd together to form a single inlet/outlet port that connects to a single supply/drain line extending outside of the chamber to the pump line or tube. The first or fresh one-way valve is oriented to only open under negative pressure to enable fresh PD fluid to be pulled from the fresh PD fluid compartment. The second or used one-way valve is oriented to only open under positive pressure to enable used PD fluid to be delivered into the used PD fluid compartment.

The PD fluid containers or bags may alternatively be configured so that the mixing of fresh and used PD fluid, which are allowed to contact each other at an interface, is reduced to a negligible amount. Here, a supply line is placed in fluid communication with a fresh PD fluid end of the container, while a drain line is placed in fluid communication with a used PD fluid end of the container. Fresh dialysis fluid is delivered from the fresh PD fluid end, through the supply line, through the patient line, to the patient. Used dialysis fluid is delivered from the patient, through the patient line, through the drain line, to the drain side of the container. A drain inlet barrier may be positioned in the drain side of the container to deflect and make laminar the flow of incoming drain fluid.

A control unit having one or more processor and memory is provided to (i) control all of the fluid valves, a bidirectional pump, the heater and (ii) receive signals from the weigh scale and other sensors, such as temperature and pressure sensors, to perform each of the pumping sequences described herein. The control unit also interfaces with a user interface. The user interface may be provided with a touch-screen and/or electromechanical pushbuttons to allow the user or patient to enter parameters for treatment and a display screen for providing information, such as treatment status information. The control unit may also communicate over a network with a doctor or clinician computer or computer system to upload treatment and compliance data and to receive device and treatment prescriptions from the doctor or clinician.

In light of the disclosure set forth herein, and without limiting the disclosure in any way, in a first aspect, which may be used with any other aspect described herein, or portion thereof, a peritoneal dialysis ("PD") system comprises a cycler including a weigh scale, a chamber positioned to be weighed by the weigh scale, a heater positioned to heat an inside of the chamber, a plurality of valves supported by the chamber or a housing of the cycler, a pump supported by the chamber or a housing of the cycler, and a control unit operable with the weigh scale, the heater, the plurality of valves and the pump; and a disposable set including a PD fluid container sized to fit within the chamber so as to be weighed by the weigh scale and heated by the heater, a supply line in fluid communication with the PD fluid container and extending outside of the chamber, a drain container sized to fit within the chamber so as to be weighed by the weigh scale, a drain line in fluid communication with the drain container and extending outside of the chamber, and a patient line positioned on an opposing side of the pump from the supply line and the drain line, wherein the control unit is configured to operate the plurality of valves and the pump bidirectionally to pump (i) used dialysis fluid from the patient line, through the drain line, to the drain container and (ii) fresh dialysis fluid from the PD fluid container, through the supply line, and through the patient line.

In a second aspect, which may be used with any other aspect described herein, or portion thereof, the plurality of valves include a supply line valve, a drain line valve and a patient line valve, wherein the control unit is configured to open the drain line valve and the patient line valve for (i) of claim 1, and wherein the control unit is configured to open the supply line valve and the patient line valve for (ii) of claim 1.

In a third aspect, which may be used with any other aspect described herein, or portion thereof, at least one of the supply line valve, drain line valve or patient line valve is a pinch valve that opens or occludes the supply line, drain line or patient line, respectively.

In a fourth aspect, which may be used with any other aspect described herein, or portion thereof, the pump is a peristaltic pump, and wherein the disposable set includes a peristaltic pumping tube located between (a) the supply line and the patient line and (b) the drain line and the patient line.

in a fifth aspect, which may be used with any other aspect described herein, or portion thereof, the PD fluid container is a first PD fluid container and the supply line is a first supply line, and which includes a second PD fluid container sized to fit within the chamber so as to be weighed by the weigh scale and heated by the heater, and a second supply line in fluid communication with the second PD fluid container and extending outside of the chamber.

In a sixth aspect, which may be used with any other aspect described herein, or portion thereof, the chamber is configured for the second PD fluid container to be placed on top of the first PD fluid container.

In a seventh aspect, which may be used with any other aspect described herein, or portion thereof, the chamber is configured for the second PD fluid container to be placed adjacent to the first PD fluid container.

In an eighth aspect, which may be used with any other aspect described herein, or portion thereof, the patient line is positioned on the opposing side of the pump from the supply line, the drain line and the second supply line.

In a ninth aspect, which may be used with any other aspect described herein, or portion thereof, the supply line mates with a container line extending from the PD fluid container.

In a tenth aspect, which may be used with any other aspect described herein, or portion thereof, the mating of the supply line and the container line occurs along a side of the chamber supporting at least one of the supply line or the container line.

In an eleventh aspect, which may be used with any other aspect described herein, or portion thereof, the chamber is configured for the supply line to extend into the chamber for connection to the PD fluid container.

In a twelfth aspect, which may be used with any other aspect described herein, or portion thereof, the disposable set further includes a terminal drain line, and wherein the control unit is further configured to operate at least some of the plurality of valves and the pump to pump used dialysis fluid from the drain container, after the used dialysis fluid is weighed by the weigh scale, to the terminal drain line.

In a thirteenth aspect, which may be used with any other aspect described herein, or portion thereof, the terminal drain line is positioned along with the patient line on the opposing side of the pump from the supply line and the drain line.

In a fourteenth aspect, which may be used with any other aspect described herein, or portion thereof, the terminal drain line extends to a terminal drain container or to a house drain.

In a fifteenth aspect, which may be used with any other aspect described herein, or portion thereof, a peritoneal dialysis ("PD") system comprises a cycler including a weigh scale, a chamber positioned to be weighed by the weigh scale, a heater positioned to heat an inside of the chamber, a plurality of valves supported by the chamber or a housing of the cycler, a pump supported by the chamber or a housing of the cycler, and a control unit operable with the weigh scale, the heater, the plurality of valves and the pump; and a disposable set including a PD fluid container sized to fit within the chamber so as to be weighed by the weigh scale and heated by the heater, the PD fluid container including a fresh PD fluid compartment and a used PD fluid compartment, a supply line in fluid communication with the fresh PD fluid compartment and extending outside of the chamber, a drain line in fluid communication with the used PD fluid compartment and extending outside of the chamber, and a patient line positioned on an opposing side of the pump from the supply line and the drain line, wherein the control unit is configured to operate the plurality of valves and the pump bidirectionally to pump (i) used dialysis fluid from the patient line, through the drain line, to the used PD fluid compartment and (ii) fresh dialysis fluid from the fresh PD fluid compartment, through the supply line, and through the patient line.

In a sixteenth aspect, which may be used with any other aspect described herein, or portion thereof. (i) the supply line mates with a fresh compartment line extending from the fresh PD fluid compartment and (ii) the drain line mates with a used compartment line extending from the used PD fluid compartment.

In a seventeenth aspect, which may be used with any other aspect described herein, or portion thereof, the chamber is configured for (i) the supply line to extend into the chamber for connection to the fresh PD fluid compartment and (ii) the drain line to extend into the chamber for connection to the used PD fluid compartment.

In an eighteenth aspect, which may be used with any other aspect described herein, or portion thereof, the chamber is sized to hold an entire fresh PD fluid volume at a beginning of a treatment and used PD fluid from multiple drains at the end of the treatment.

In a nineteenth aspect, which may be used with any other aspect described herein, or portion thereof, a peritoneal dialysis ("PD") system comprises a cycler including a weigh scale, a chamber positioned to be weighed by the weigh scale, a heater positioned to heat an inside of the chamber, a plurality of valves supported by the chamber or a housing of the cycler, a pump supported by the chamber or a housing of the cycler, and a control unit operable with the weigh scale, the heater, the plurality of valves and the pump; and a disposable set including a PD fluid container sized to fit within the chamber so as to be weighed by the weigh scale and heated by the heater, the PD fluid container including a fresh PD fluid compartment and a used PD fluid compartment, a first one-way valve in fluid communication with the fresh PD fluid compartment, the first one-way valve oriented to open under negative pressure from outside the fresh PD fluid compartment, a second one-way valve in fluid communication with the used PD fluid compartment, the second one-way valve oriented to open under positive pressure from outside the used PD fluid compartment, a supply/drain line in fluid communication with the first and second one-way valves, the supply/drain line extending outside of the chamber, and a patient line positioned on an opposing side of the pump from the supply/drain line, wherein the control unit is configured to operate the plurality of valves and the pump bidirectionally to pump (i) used dialysis fluid from the patient line, through the supply/drain line and the second one-way valve, to the used PD fluid compartment and (ii) fresh dialysis fluid from the fresh PD fluid compartment, through the first one-way valve and the supply/drain line, through the patient line.

In a twentieth aspect, which may be used with any other aspect described herein, or portion thereof, wherein the supply/drain line mates with a tee extending to a first port holding the first one-way valve and a second port holding the second one-way valve.

In a twenty-first aspect, which may be used with any other aspect described herein, or portion thereof, the chamber is sized to hold an entire fresh PD fluid volume at a beginning of a treatment and used PD fluid from multiple drains at the end of the treatment.

In a twenty-second aspect, which may be used with any other aspect described herein, or portion thereof, a peritoneal dialysis ("PD") system comprises a cycler including a weigh scale, a chamber positioned to be weighed by the weigh scale, a heater positioned to heat an inside of the chamber, a plurality of valves supported by the chamber or a housing of the cycler, a pump supported by the chamber or a housing of the cycler, and a control unit operable with the weigh scale, the heater, the plurality of valves and the pump; and a disposable set including a PD fluid container sized to fit within the chamber so as to be weighed by the weigh scale and heated by the heater, the PD fluid container including a fresh PD fluid end and a used PD fluid end, a supply line in fluid communication with the fresh PD fluid end and extending outside of the chamber, a drain line in fluid communication with the used PD fluid end and extending outside of the chamber, and a patient line positioned on an opposing side of the pump from the supply line and the drain line, wherein the control unit is configured to operate the plurality of valves and the pump bidirectionally to pump (i) used dialysis fluid from the patient line, through the drain line, to the used PD fluid end of the PD fluid container and (ii) fresh dialysis fluid from the fresh PD fluid end of the PD fluid container, through the supply line, and through the patient line.

In a twenty-third aspect, which may be used with any other aspect described herein, or portion thereof. (i) the supply line mates with a fresh compartment line extending from the fresh PD fluid end of the PD fluid container and (ii) the drain line mates with a used compartment line extending from the used PD fluid end of the PD fluid container.

In a twenty-fourth aspect, which may be used with any other aspect described herein, or portion thereof, the chamber is configured for the (i) supply line to extend into the chamber for connection to the fresh PD fluid end of the PD fluid container and (ii) the drain line to extends into the chamber for connection to the used PD fluid end of the PD fluid container.

In a twenty-fifth aspect, which may be used with any other aspect described herein, or portion thereof, the used PD fluid end of the PD fluid container includes a drain inlet barrier for dampening incoming used PD fluid flow.

In a twenty-sixth aspect, which may be used with any other aspect described herein, or portion thereof, fresh PD fluid and used PD fluid within the PD fluid container meet at a fresh/used PD fluid interface.

In a twenty-seventh aspect, any of the features, functionality and alternatives described in connection with any one or more of FIGS. 1 to 12 may be combined with any of the features, functionality and alternatives described in connection with any other of FIGS. 1 to 12.

It is accordingly an advantage of the present disclosure to provide an automated peritoneal dialysis ("APD") cycler that is massed balanced to provide needed accuracy to control fill and drain volumes and the difference between fill and drain volumes.

It is another advantage of the present disclosure to provide an APD cycler that uses a relatively simple disposable set.

It is a further advantage of the present disclosure to provide a relatively quiet APD cycler.

It is still another advantage of the present disclosure to provide an APD cycler that is relatively cost effective.

It is yet a further advantage of the present disclosure to provide an APD system that is relatively easy to setup and use.

It is yet another advantage of the present disclosure to provide an APD system that employs a relatively low cost disposable set.

It is still another advantage of the present disclosure to hold fresh PD fluid supply containers inside of a chamber so that they are contained within the overall system.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
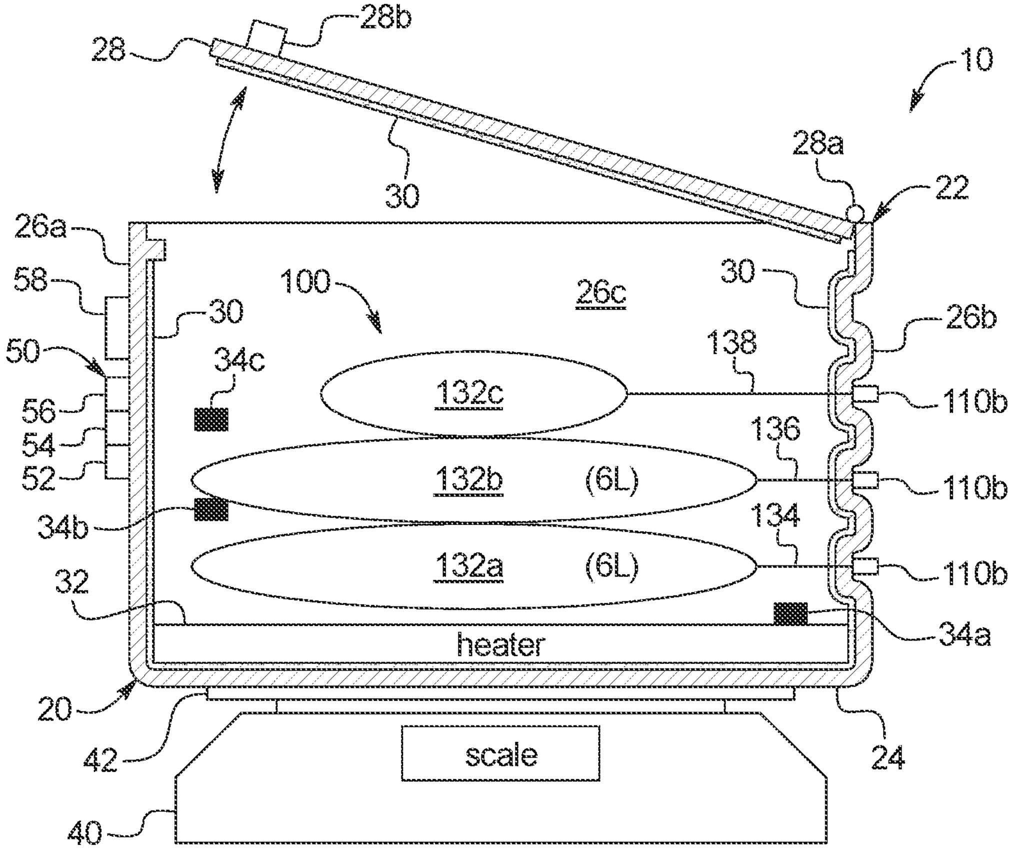
FIG. 1 is a sectioned elevation view of one embodiment of the automated peritoneal dialysis ("APD") cycler of the present disclosure having an insulated chamber that holds multiple dialysis fluid containers, and which sits atop a weigh scale for monitoring fresh and used dialysis fluid delivery.
Figure 2:
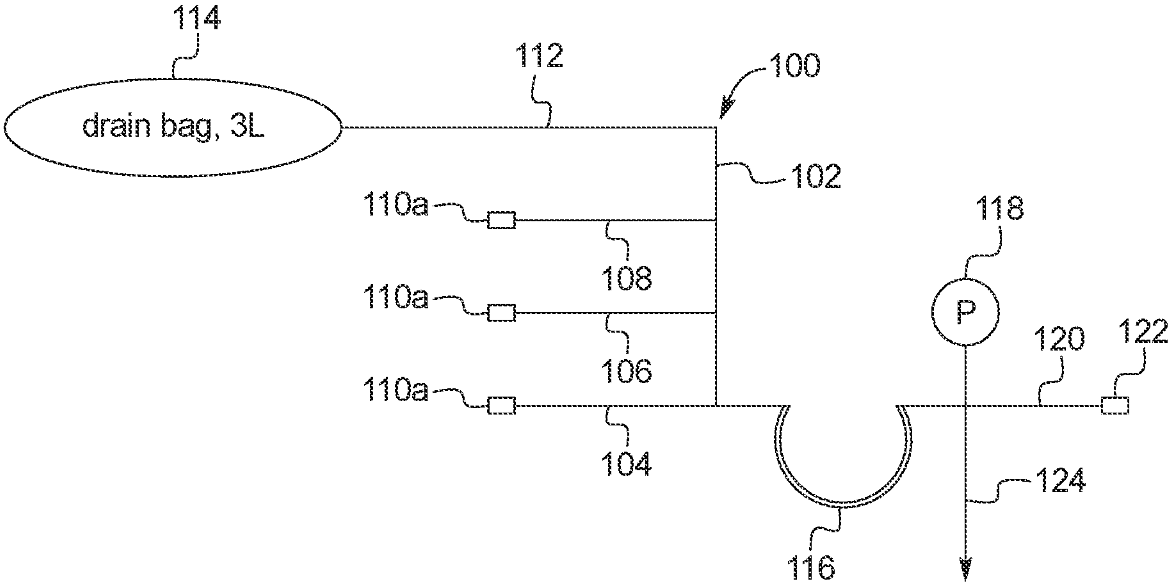
FIG. 2 is a plan view of one embodiment of a disposable set used with the APD cycler of the present disclosure.

Referring now to the drawings and in particular to FIGS. 1 and 2, an automated peritoneal dialysis ("APD") system 10 includes and APD machine or cycler 20 that operates with a disposable set 100 (shown also in FIG. 2. FIG. 1 illustrates fluid containers and corresponding fluid lines of disposable set 100). APD machine or cycler 20 includes a chamber 22, which may be an insulated chamber and a rigid structure that accepts a portion (fluid containers and corresponding fluid lines) of disposable set 100. Chamber 22 may be made of plastic, such as, polyvinyl chloride ("PVC"), polyethylene ("PE") or polyurethane ("PU"), polycarbonate ("PC") or of metal, such as stainless steel, steel or aluminum. Chamber 22 may be reusable or disposable but in order to reduce disposable material and cost is generally considered to be reusable. Chamber 22 may also be insulated either by being constructed of a thermally insulated material and/or by being lined with a thermally insulated liner.

Disposable set 100, including all tubing, connectors and containers or bags, is made of a medically safe material such as PVC or a non-PVC material, such as one of the polymers listed above. FIG. 2 illustrates an initially dry portion of disposable set 100, while FIG. 1 illustrates dialysis fluid containers or bags that are initially filled with fluid. It should be appreciated that while disposable set 100 is illustrated as including the components shown in both FIGS. 1 and 2, which may be packaged connected together or disconnected from each other, in an alternative embodiment, disposable set 100 may include the containers of FIG. 1 provided in separate sterilized containers and the tubes or lines of FIG. 2 provided collectively in a separate sterilized overpouch.

The initially wet portion of disposable set 100 shown in FIG. 1 includes dialysis fluid containers or bags 132*a* to 132*c* and container lines 134, 136, 138 leading from containers or bags 132*a*, 132*b* and 132*c*, respectively, to supply container connectors 110*b*, which mate each with a supply line connector 110*a*. Containers or bags 132*a*, 132*b* and 132*c* may contain the same or different types (formulations) and/or volumes of peritoneal dialysis ("PD") fluid. Containers or bags 132*a* and 132*b* may, for example, be used for multiple fills during a treatment and hold, e.g., six liters each of a first formulation of PD fluid. Container or bag 132*c* may, for example, contain a last fill volume's worth of icodextrin, which is specially formulated to remain within the patient until the next treatment or perhaps until a day exchange. In an alternative embodiment, container lines 134, 136, 138 leading from containers or bags 132*a*. 132*b* and 132*c* are not provided and supply container connectors 110*b* are provided instead as ports extending from containers or bags 132*a*. 132*b* and 132*c*.

As illustrated in FIG. 1, chamber 22 includes a bottom 24, sides 26*a* to 26*c*, a surface on the page (cutaway to see inside) and a lid or top 28. Lid 28 is hinged to side 26*b* via a hinge 28*a*, which may be a living hinge or separate hinge, wherein lid 28 lifted by the patient or caregiver via handle 28*b*. At least a portion of sides 26*a* to 26*c* (and front surface) and lid 28 may be covered and lined with a thermally insulated liner 30, such as a fabric, rubber or foam. Chamber 22 may be generally rectangular as illustrated or be provided in any desired shape, e.g., to conform in a spacewise efficient manner to the overall shape defined by the containers or bags held within chamber 22.

Cycler 20 may include a heater 32, such as an electrical plate heater, which is located inside of chamber 22, e.g., supported by the bottom 24 of the chamber. One or more temperature sensor 34*a* to 34*c* is positioned to measure any one or more of (i) the temperature of heater 32 (34*a*), (ii) the surface temperature of any one or more or all of the dialysis fluid containers or bags located within chamber 22 (34*b*), and/or (iii) the air temperature within chamber 22 (34*c*). The output of any one or more temperature sensor 34*a* to 34*c* may be used as feedback to a control unit 50 controlling heater 32 and/or for a display on a user interface 58 of system 10.

FIG. 1 also illustrates that cycler 20 may include a weigh scale 40 having a weighing pan 42 supporting chamber 22, e.g., from underneath the bottom 24 of the chamber. Chamber 22 in the embodiments illustrated herein is sized to hold all of the fresh and used dialysis fluid (at least temporarily) over the course of treatment. Weigh scale 40 may accordingly monitor the amount of fresh and used dialysis fluid delivered during any patient fill or patient drain of a treatment using system 10, including an initial patient drain. Weigh scale 40 may include one or more load cell, strain gauge and/or other type of force sensor. The output from weight scale 40 may also be displayed on a user interface 58 of system 10.

FIG. 1 illustrates the control unit 50 of system 10, which in the illustrated embodiment is located on the outside of chamber 22 (or a cycler housing holding chamber 22), e.g., to isolate control unit 50 from any heat generated within the chamber, although the heat generated from plate heater 32 is not expected to be extensive. Control unit 50 may alternatively be provided as a wireless user interface, such as a tablet or smartphone. In any case, as illustrated in FIG. 1, control unit 50 may include one or more processor 52, one or more memory 54, and a video controller 56 interfacing with user interface 58, which may include a display screen operating with a touchscreen and/or one or more electromechanical button, such as a membrane switch. User interface 58 may also include one or more speaker for outputting alarms, alerts and/or voice guidance commands. Control unit 50 may further include a transceiver and a wired or wireless connection to a network, e.g., the internet, for sending treatment data to and receiving prescription instructions from a doctor's or clinician's server interfacing with a doctor's or clinician's computer.

FIG. 2 illustrates one embodiment of an initially dry portion of disposable set 100. Disposable set 100 in FIG. 2 includes a common or manifold line 102. Supply lines 104, 106 and 108 extend from manifold line 102, each terminating at a supply line connector 110*a*. A drain line 112 extends from manifold line 102 to an initially dry drain container or bag 114, which may for example be sized to hold a single patient drain's worth of effluent, e.g., three liters, or alternatively multiple drain's worth of effluent. A peristaltic pumping tube 116 is provided and may be of a different material, e.g., silicone, and hardness than the rest of the tubing of disposable set 100. Peristaltic pumping tube 116 on one end is in fluid communication with manifold line 102 and thus supply lines 104, 106 and 108 and drain line 112. Peristaltic pumping tube 116 on the other end is in fluid communication with a pressure sensing pod 118, a patient line 120 extending to a patient connector 122 for connecting to the patient's transfer set, and a terminal drain line 124 for ultimately removing used dialysis fluid including the patient's ultrafiltration ("UF") to a drain container or house drain (e.g., toilet, bathtub or sink).

Figure 3:
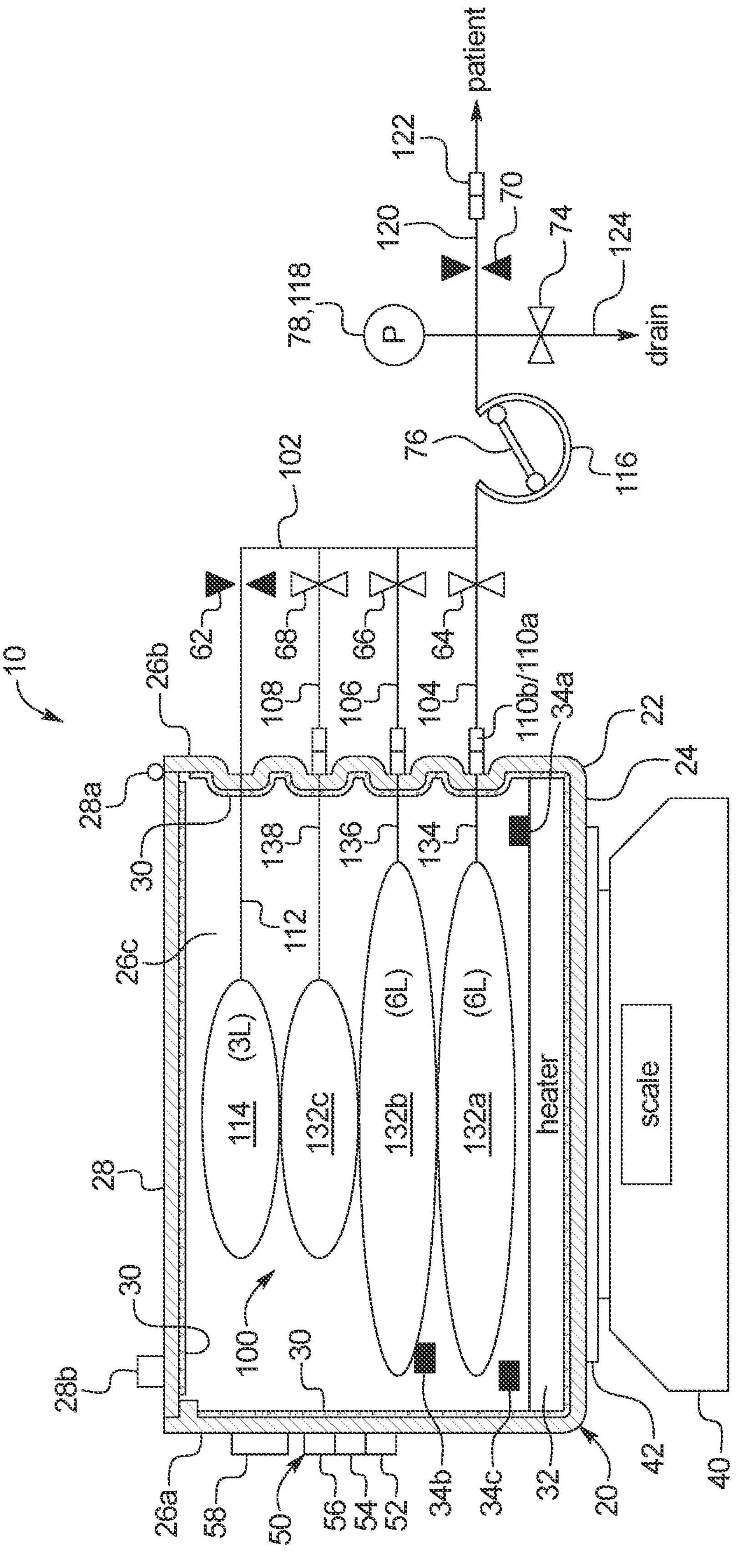
FIG. 3 is a sectioned elevation view of one embodiment of the APD cycler of the present disclosure performing an initial (or subsequent) patient drain.

Referring now to FIG. 3, it is illustrated that for treatment setup, the patient or caregiver loads containers or bags 132*a*, 132*b* and 132*c* into chamber 22, loads drain container or bag 114 onto last fill container 132*c*, and connects supply line connectors 110*a* to supply container connectors 110*b*. Supply line connectors 110*a* and supply container connectors 110*b* may be color coded and/or keyed to ensure that the correct connections are made. The patient or caregiver also places pressure sensing pod 118 into operable communication with a pressure transducer of cycler 20, which outputs to control unit 50.

FIG. 3 also illustrates that cycler 20 includes valves 62, 64, 66 and 68 that operate to open and occlude drain line 112, and supply lines 104, 106 and 108, respectively. A fifth valve 70 opens and occludes patient line 120, while a sixth valve 74 opens and occludes terminal drain line 124. Valves 62, 64, 66, 68, 70 and 74 may be electrically actuated solenoid pinch valves (or any other suitable type of valve), under control of control unit 50, which may be energized open and deenergized closed for fail safe operation. The valves close their respective line or tube to occlude the line and open to allow fresh or used PD fluid flow.

A peristaltic pump actuator 76 is operable in clockwise and counterclockwise directions to pump fresh and used dialysis fluid through peristaltic pumping tube 116. Peristaltic pump actuator 76 may for example include an electrically actuated stepper motor that moves a peristaltic pump rotor, which pinches peristaltic pumping tube 116 against a raceway to drive fluid in a desired direction. Pressure sensing pod 118 operates with pressure transducer 78. Each of control unit 50, user interface 58, valves 62, 64, 66, 68, 70 and 74, peristaltic pump actuator 76 and pressure transducer 78 may be located, for example, on the outer surface of one or more of sides 26*a* to 26*c* of chamber 22, the surface on the page (cutaway to see inside the chamber), and/or lid 28. In the illustrated example, control unit 50 and user interface 58 may be located on the outer surface of side 26*a*, while valves 62, 64, 66, 68, 70 and 74, peristaltic pump actuator 76 and pressure transducer 78 are located on the outer surface of side 26*b*. Alternatively, each of the structures is located on the same side of chamber 22. In an embodiment, peristaltic pump actuator 76 is located so that patient line 120 is prevented from tugging or pulling on chamber 22, which may affect the reading of scale 40. For example, a service loop or other type of strain relief structure may be provided in the tubing on one or both sides of peristaltic pump actuator 76.

Each of temperature sensors 34*a* to 34*c*, heater 32, valves 62, 64, 66, 68, 70 and 74, peristaltic pump actuator 76 and pressure transducer 78 is under the control of and/or outputs to control unit 50. Although it may not be explicitly stated below, control unit 50 may control any of the valve states and peristaltic pump actuations described herein. Control unit 50 receives output signals from any one or more temperature sensor 34*a* to 34*c* to use as feedback to control heater 32 so as to heat fresh dialysis fluid within container or bags 132*a* to 132*c* to body temperature or 37° C. Control unit 50 receives output signals from pressure transducer 78 to use as feedback to control the speed of peristaltic pump actuator 76 so as to maintain any patient pumping within a safe pressure limit, e.g., within one to five psig for patient fills (e.g., two psig (14 kPa)) and −1.0 to −3.0 psig (e.g., 1.3 psig (−9 kPa)) for patient drains. Draining from drain container or bag 114 through terminal drain line 124 to a final drain container or house drain may be performed at higher pressures and flowrates because it does not involve the patient. Control unit 50 may employ proportional, integral and derivative ("PID") control for either one or both of PD fluid temperature and pumping pressure.

FIG. 3 illustrates a situation at the beginning of treatment when the patient is full of effluent from a previous treatment and all three PD fluid containers or bags 132*a* to 132*c* are full of fresh fluid. Here, at least the PD fluid in lower container 132*a* is heated to body temperature. An initial drain is performed in which used PD fluid from the previous treatment's last fill, with valves 62 and 70 open (pinch arrows pulled apart in FIG. 3) and peristaltic pump actuator 76 operating in a clockwise direction, is pulled from the patient and pushed into drain container or bag 114. The initial (and any) patient drain stops in one embodiment when pressure transducer 78 senses a characteristic change (e.g., drop) in negative pressure, indicating that the patient is or is near empty. The amount of the initial patient drain, including fluid removed from that patient, is sensed by scale 40 and delivered to control unit 50. That amount may either be included in the present treatment's total UF calculation (total used fluid removed from the patient less total fresh fluid delivered to the patient) or may be included in the previous treatment's total UF calculation (total used fluid removed from the patient less total fresh fluid delivered to the patient), in which case the next treatment's initial drain is included in the present treatment's total UF calculation.

It is quite possible that the patient is not full of used dialysis fluid or effluent at the beginning of treatment. In such a case, treatment begins with a patient fill. It is also possible that the patient does not receive a last fill at the end of treatment (e.g., if the last fill PD fluid container or bag 132*c* is not provided or if the patient has drained some time during the day). It should be appreciated however that control unit 50 may be configured to default to attempting a patient drain (safety drain) at the beginning of each treatment in case the patient may have forgotten to perform a drain at the end of a previous treatment or from an exchange in between treatments.

In any case, it is contemplated to prime disposable set 100 prior to the first patient fill. For priming, control unit 50 causes each supply valve 64, 66 and 68 and final drain valve 74 to be opened and peristaltic pump actuator 76 to operate in a counterclockwise direction to pull fresh PD fluid from each of PD fluid containers 132*a* to 132*c*, which in turn drives air in lines 134/104, 136/106, 138/108 and 102 into terminal drain line 124, to a terminal drain container or house drain. Control unit 50 in an embodiment sequences supply valves 64, 66 and 68 and drain valve 74 open so that control unit 50 can confirm via signals from weigh scale 40 that fluid has traveled to each of the valves. The amount of fresh PD fluid needed and delivered here may be known via corresponding tubing volume and controlled via a corresponding weight sensed by weigh scale 40, e.g., plus an engineering factor of additional PD fluid. It should be appreciated that an initial drain could be used to prime patient line 120, manifold line 102 and drain line 112, pushing air into drain container or bag 114, after which the above priming sequence pushes much of the effluent priming fluid to terminal drain. It may however be prudent not to rely on an initial patient drain for priming, e.g., in case the patient has less effluent to drain than expected. Here, or if an initial drain is not provided, patient line 120 may be primed with fresh PD fluid up to a hydrophobic membrane provided with patient connector 122, or up to a prime sensor (e.g., optical, capacitive or other) outputting to control unit 50 and against which patient connector 122 at the end of patient line 120 is located prior to treatment.

Figure 4:
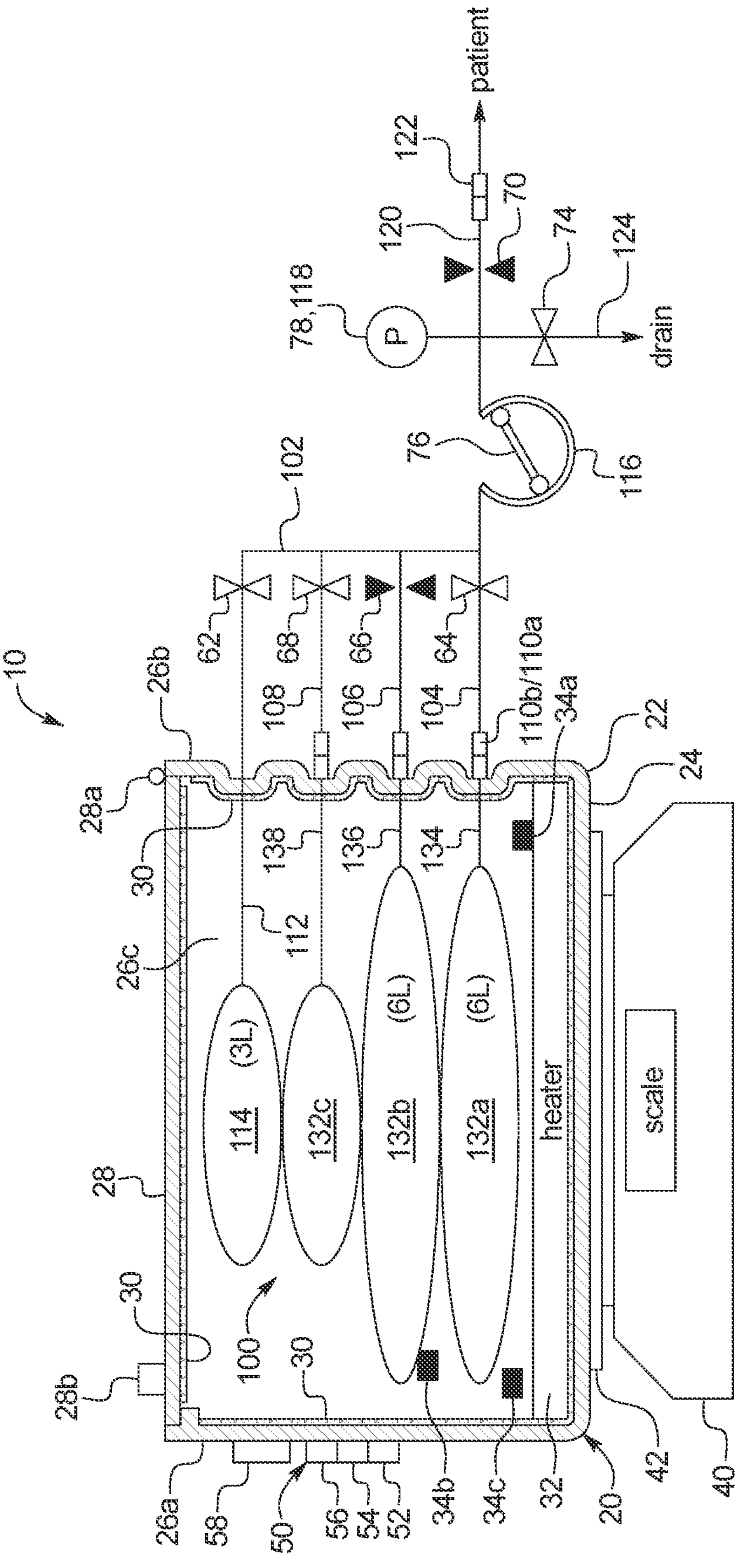
FIG. 4 is a sectioned elevation view of one embodiment of the APD cycler of the present disclosure performing a patient dwell.

FIG. 4 illustrates a patient fill in which control unit 50 causes supply valve 66 and patient valve 70 to be open (pinch arrows pulled apart in FIG. 4) and peristaltic pump actuator 76 to operate in a counterclockwise direction to pull fresh dialysis fluid from PD fluid container 132*b* and push same through patient line 120 to the patient. Control unit 50 may cause supply valve 64 to be opened first so that lowest container 132*a* is consumed first, after which supply valve 66 for second lowest container 132*b* is opened as illustrated in FIG. 4 for a subsequent patient fill. Assuming each fluid container 132*a* and 132*b* is heated up to body temperature or 37° C., fresh PD fluid may be pulled from either container and from each container multiple times. If fluid containers 132*a* and 132*b* contain different glucose or dextrose level dialysis fluids, supply valves 64 and 66 may be sequenced to allow different PD fluids to be provided over different patient fills of a treatment, e.g., according to a prescribed patient prescription. Supply valves 64 and 66 may also be toggled via control unit 50 during a same patient fill to achieve an accurately weighed blend of PD fluid as may be called for by the patient's prescription. All patient fills of a treatment are completed and stopped in one embodiment when weigh scale 40 records a prescribed patient fill volume's worth of fresh PD fluid as having left one or more of fluid containers 132*a* to 132*c*. Patient fill volumes may be the same or different for different patient fills of a treatment according to the patient's prescription.

Figure 5:
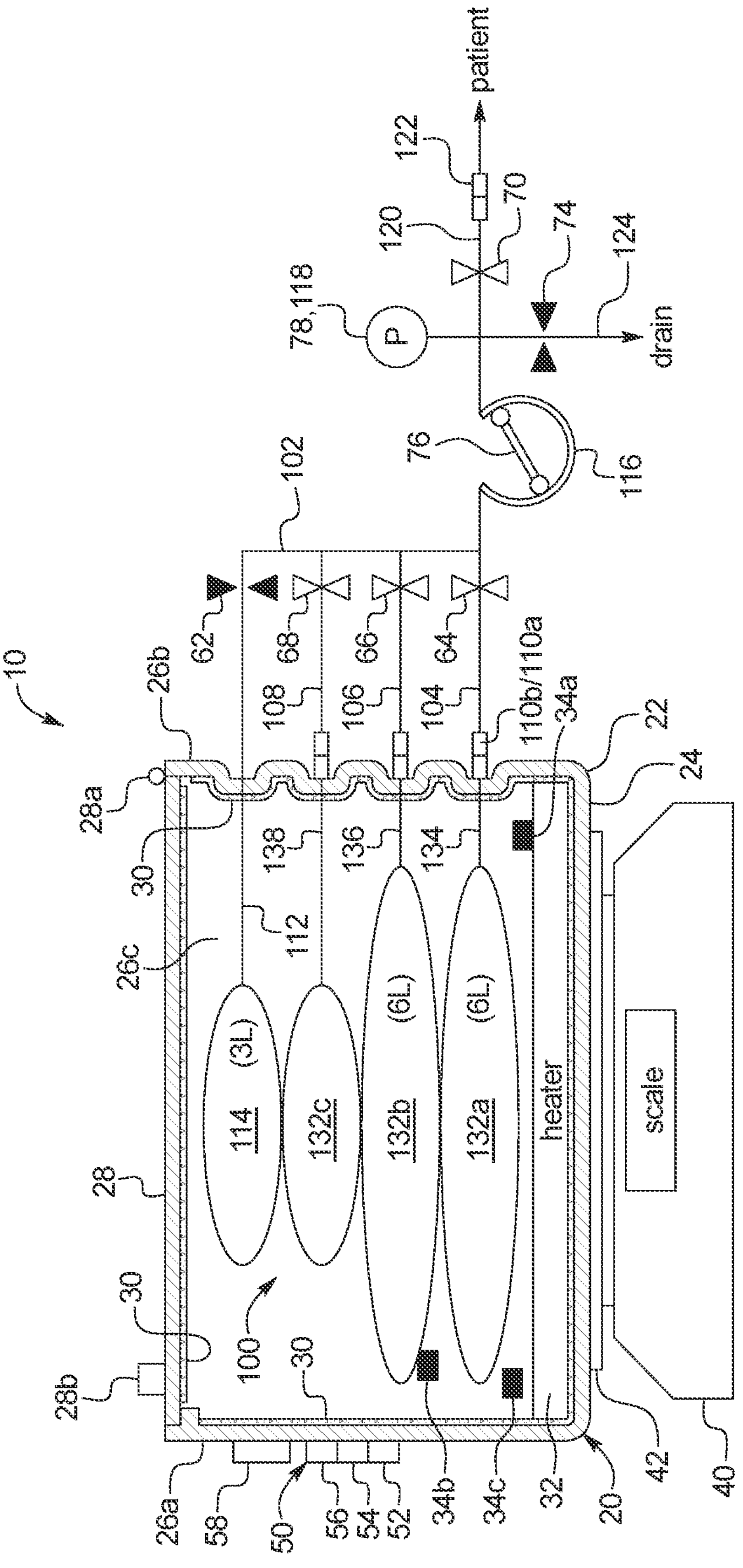
FIG. 5 is a sectioned elevation view of one embodiment of the APD cycler of the present disclosure performing a patient fill.

FIG. 5 illustrates one embodiment of a patient dwell, which may last on the order of one or more hour. During this time period, control unit 50 may perform one or a number of procedures to prepare for the next patient drain and patient fill. For example, control unit 50 may continue to heat a next PD fluid container 132*a* to 132*c* so that it is ready as soon as the next patient drain is completed. Control unit 50 in one embodiment during the patient dwell also removes used dialysis fluid from drain container 114 to the terminal drain. Here, control unit 50 causes drain valves 62 and 74 to be open (pinch arrows pulled apart in FIG. 5) and peristaltic pump actuator 76 to operate in a counterclockwise direction to pull used dialysis fluid from drain container 114 and push same through drain line 112, manifold line 102, and terminal drain line 124 to a terminal drain container or house drain. As discussed above, such pumping may be performed at an increased pressure and flowrate because the patient is not involved. Control unit 50 may cause final draining to occur until the weight of effluent or used dialysis fluid previously received within drain container 114 is recorded and outputted by weigh scale as having been removed from the drain container. In an alternative embodiment, cycler 20 may provide an air sensor (e.g., optical or capacitive) to detect air, e.g., in common or manifold line 102, after all effluent has been removed from drain container 114.

Figure 6A:
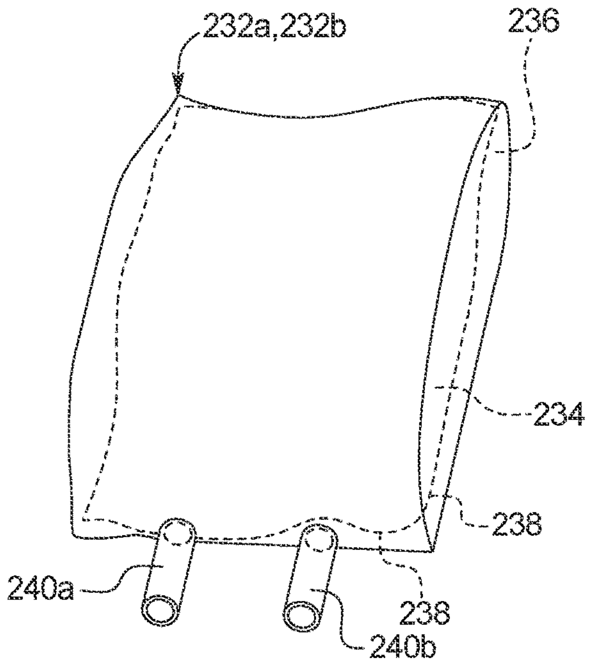
FIG. 6A is a perspective view of one embodiment of a first alternative dialysis fluid container of the present disclosure, which provides a second compartment for collecting used dialysis fluid or effluent from the patient.

Referring now to FIG. 6A, a first alternative PD fluid container or bag 232*a*. 232*b* is illustrated. First alternative PD fluid container or bag 232*a*, 232*b* may be made of any of the polymer materials discussed herein and includes two compartments 234 and 236, which are separated by an intermediate plastic or polymer layer 238. First compartment 234 holds fresh PD fluid, which may be sterilized for use along with PD fluid container or bag 232*a*, 232*b*, e.g., via steam sterilization or gamma radiation. A second, used PD fluid compartment 236 of at least one of containers 232*a*, 232*b* is empty and is sized to hold an initial drain volume's worth of effluent, e.g., up to three liters, and which includes used dialysis fluid and patient ultrafiltration ("UF"). In one embodiment, the second compartments 236 of both containers 232*a*, 232*b* are each empty and are sized to hold multiple drain volume's worth of effluent. For example, first compartments 234 of both containers 232*a*, 232*b* may be sized to hold six liters of fresh PD fluid, while second compartments 236 of both containers 232*a*, 232*b* are empty initially and are sized to hold the entire drain volume produced via the six liters of fresh PD from first compartment 234. It may be possible in an alternative embodiment for the second, used PD fluid compartment 236 of one of containers 232*a*, 232*b* to be initially full of fresh PD fluid and then used as a drain compartment after it is emptied.

FIG. 6A illustrates that compartment 234 of container 232*a*, 232*b* includes and fluidly communicates with a fresh port 240*a* for connecting to a container line 134 or 136, while compartment 236 includes and fluidly communicates a drain port 240*b* for connecting to a drain line segment of an alternative disposable set 200 (FIGS. 8 and 10 to 12). Fresh port 240*a* and drain port 240*b* enable compartments 234 and 236 to be independently drained and filled, respectively.

Figure 6B:
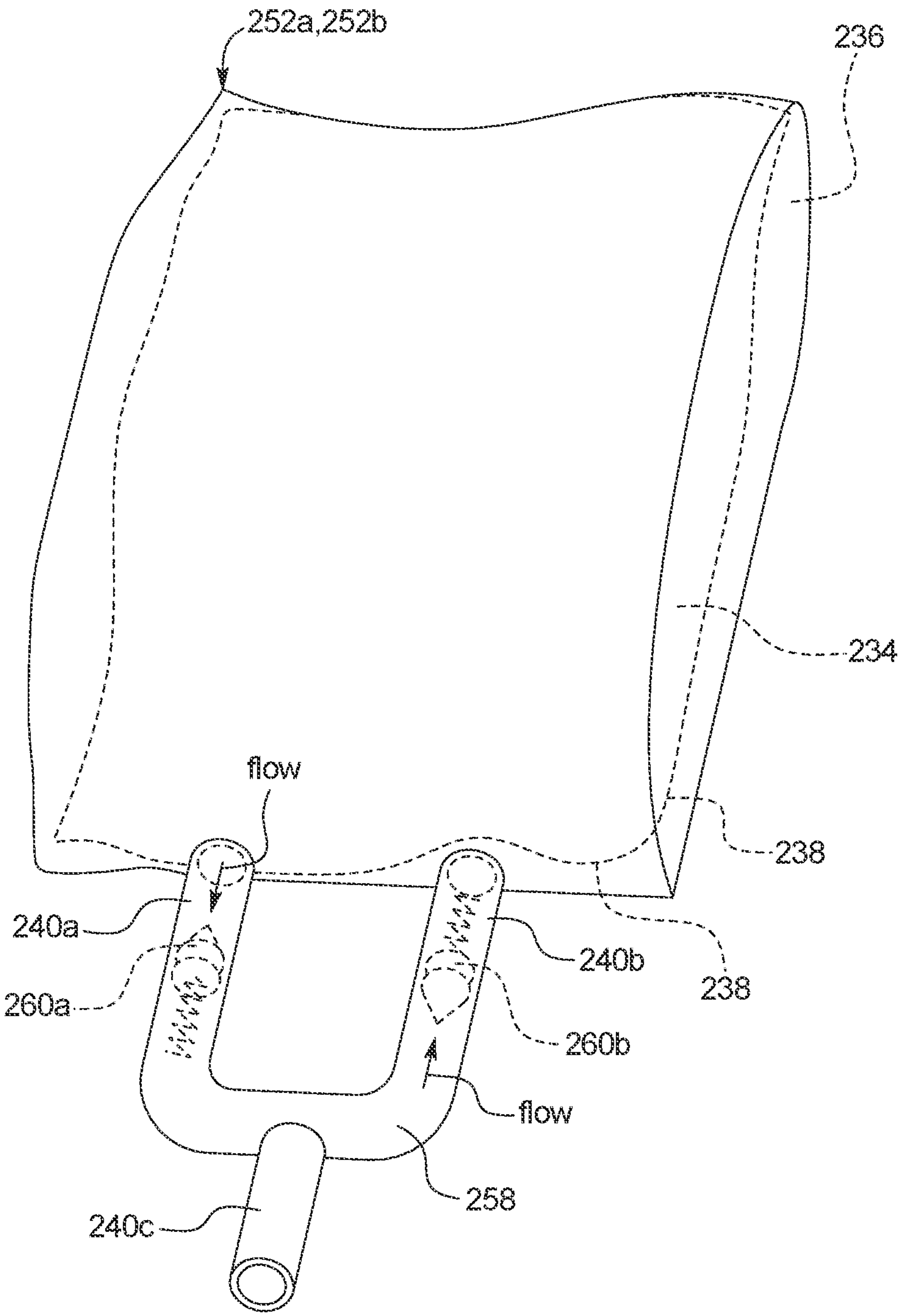
FIG. 6B is a perspective view of one embodiment of a second alternative dialysis fluid container of the present disclosure, which provides a second compartment for collecting used dialysis fluid or effluent from the patient.

FIG. 6B illustrates container 252*a*, 252*b* which is an alternative version to container 232*a*, 232*b*. Container 252*a*, 252*b* is made of any of the materials discussed herein and includes each of the features of container 232*a*, 232*b* including fresh PD fluid compartment 234 and used PD fluid compartment 236, which are separated by intermediate plastic or polymer layer 238. Container 252*a*, 252*b* also includes fresh PD fluid port 240*a* and drain port 240*b* that enable compartments 234 and 236 to be independently drained and filled, respectively. Container 252*a*, 252*b* additionally includes a tee 258 that fluidly merges fresh port 240*a* and drain port 240*b* into a single inlet/outlet port 240*c*.

In the illustrated embodiment, fresh PD fluid port 240*a* is fitted with a check valve or one-way valve 260*a* (e.g., duck-billed check valve) that is oriented to open only under negative PD fluid pressure and to remain closed under positive PD fluid pressure. Here, one-way valve 260*a* is pressure closed shut when used PD fluid is delivered to container 252*a*, 252*b* but opens under negative pressure to enable fresh PD fluid to be pulled from fresh PD fluid compartment 234 during a patient fill. Used PD fluid port 240*b* is in turn fitted with a check valve or one-way valve 260*b* (e.g., duck-billed check valve) that is oriented to open only under positive PD fluid pressure and to remain closed under negative PD fluid pressure. Here, one-way valve 260*b* remains closed when fresh PD fluid is pulled from container 252*a*, 252*b* but opens under positive pressure to enable used PD fluid to be pushed into used PD fluid compartment 236 during a patient drain.

Figure 7:
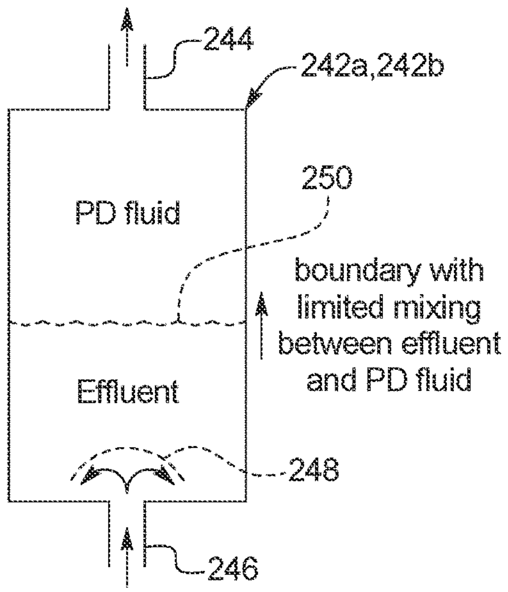
FIG. 7 is a top plan view of one embodiment of an alternative dialysis fluid container of the present disclosure, which allows used dialysis fluid or effluent from the patient to be collected.

FIG. 7 illustrates another alternative PD fluid container or bag 242*a*, 242*b*, which may be made of any of the polymer materials discussed herein. Second alternative PD fluid container or bag 242*a*, 242*b* operates under a principal of limited mixing. PD fluid container or bag 242*a*, 242*b* includes a fresh PD fluid outlet port 244 and a used dialysis fluid inlet port 246, which in the illustrated embodiment are provided on opposite ends (fresh PD fluid end versus used PD fluid end) of the container 242*a*, 242*b*. A drain inlet barrier 248, e.g., rigid plastic, is located inside PD fluid container or bag 242*a*, 242*b* and is constructed (e.g., cup or U-shaped as illustrated) and arranged (e.g., near used dialysis fluid inlet port 246) to deflect and dampen the incoming flow of used dialysis fluid. The dampened flow of used dialysis fluid tends to be more laminar and to mix less at a fresh/used PD fluid interface 250 with fresh PD fluid also contained within container or bag 242*a*, 242*b*. Two or more (e.g., staggered) drain inlet barriers 248 may be provided if desired.

PD fluid container or bag 242*a*, 242*b* may be provided in a size allowing for a three liter initial patient drain, e.g., as an overall nine liter container assuming the container holds six liters of fresh PD fluid. PD fluid container or bag 242*a*, 242*b* may be packaged with the additional material rolled-up or otherwise pressed closed to mitigate the amount of air that needs to be displaced when an initial drain volume is introduced. It may be that only an initial one of PD fluid containers or bags 242*a*, 242*b* needs to be provided with an additional empty volume for an initial drain. That is, when the first operation using the second one of PD fluid containers or bags 242*a*, 242*b* is a patient fill, space is created for a subsequent drain, so an initial free space is not needed. If the patient's therapy does not call for an initial drain then none of PD fluid containers or bags 242*a*, 242*b* needs to be provided with an additional empty volume for an initial drain.

Figure 8:
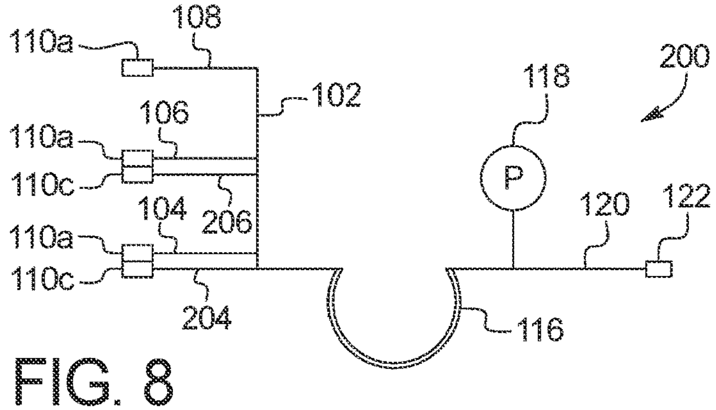
FIG. 8 is a plan view of another embodiment of a disposable set used with APD cycler of the present disclosure and with either of the alternative containers of FIG. 6A or 7.

FIG. 8 illustrates one embodiment of an initially dry portion of alternative disposable set 200. Disposable set 200 in FIG. 8 includes a manifold line 102 described above for disposable set 100. Supply lines 104, 106 and 108 extend from manifold line 102, each terminating at a supply line connector 110*a*. Drain line 112 and the initially dry drain container or bag 114 provided with disposable set 100 are not needed here, but may be provided anyway so that (i) when the treatment is finished and the patient has disconnected from disposable set 200, the patient may start a draining cycle of the entire disposable set so that the patient does not need to carry or transport the effluent containers to a toilet or other house drain for manual draining or (ii) during dwell cycler 20 may automatically drain as much effluent as possible to a house drain so that the patient does not have to wait to drain all bags at the end of treatment. Peristaltic pumping tube 116 is provided and may be of a different material, e.g., silicone, and hardness as the rest of the tubing of disposable set 200. Peristaltic pumping tube 116 is on one end in fluid communication with manifold line 102 and thus supply lines 104, 106 and 108. Peristaltic pumping tube 116 on the other end is in fluid communication with a pressure sensing pod 118 and a patient line 120 extending to a patient connector 122 for connecting to the patient's transfer set. Terminal drain line 124 provided in disposable set 100 is not needed here (but may be provided anyway for the reasons above) because drain fluid is stored instead in disposable set 200.

Alternative disposable set 200 also includes drain line segments 204 and 206 extending from manifold line 102 adjacent to supply lines 104 and 106, respectively. Drain line segments 204 and 206 each terminate at a drain line connector 110*c*. Supply line connector 110*a* and drain line connector 110*c* are illustrated as being provided together, e.g., within one housing having separate connection heads, but can alternatively be provided as separate connectors located adjacent to each other. Supply lines 104, 106 and 108 are used for patient fills of a treatment, while drain line segments 204 and 206 are used for patient drains.

For use with container 252*a*, 252*b* of FIG. 6B, alternative disposable set 200 is modified to remove either one of the supply or drain line segments and associated connectors. For example, drain line segments 204 and 206 and associated connectors 110*c* may be removed. Supply lines 104, 106 remain and double as drain lines.

Figure 9:
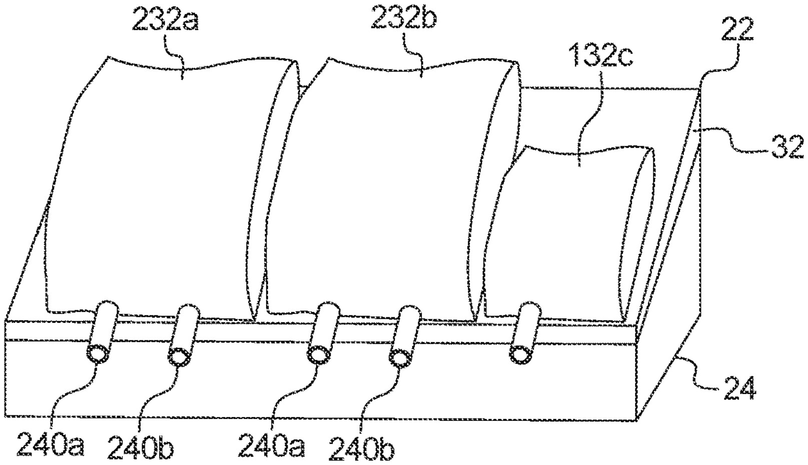
FIG. 9 is a perspective view of an alternative embodiment for placing the dialysis fluid containers into the insulated chamber of the present disclosure.

FIG. 9 illustrates an alternative arrangement for chamber 22, wherein cycler 20 is sectioned to show bottom 24 and heater 32. Alternative chamber 22 may be used with either disposable set 100 or 200, and is illustrated here as operation with PD fluid containers or bags 232*a*, 232*b*, but may be used with any of the PD fluid containers discussed herein. If it is found that stacking the PD fluid containers vertically as illustrated in FIGS. 1 and 3 to 5 does not heat each of the containers properly or homogeneously, the PD fluid containers may be loaded instead side-by-side as illustrated in FIG. 9. In the illustrated embodiment, each of PD fluid containers or bags 232*a*, 232*b* and last fill container 132*c* are heated directly by heater 32. A temperature sensor (not illustrated) outputting to control unit 50 may be located beneath any one, or more or all of PD fluid containers or bags 232*a*, 232*b* and last fill container 132*c*. In the illustrated embodiment, heater 32 is tilted so that PD fluid containers or bags 232*a*, 232*b* and last fill container 132*c* are angled for treatment. Fresh ports 240*a* and drain ports 240*b* accordingly point downwardly to help ensure that any air or gas present in the containers or does not reach the ports. Air tends to collect at the elevated tops of PD fluid containers or bags 232*a*, 232*b*. 132*c*.

Figure 10:
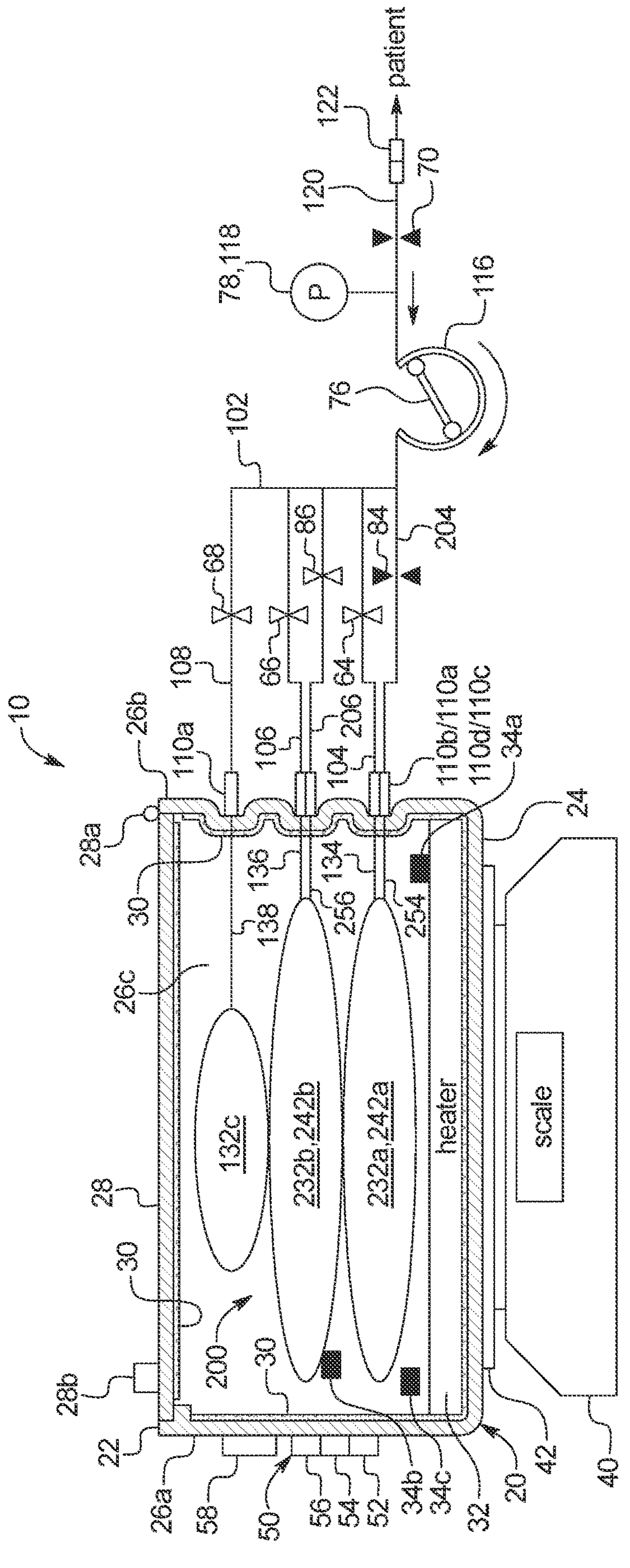
FIG. 10 is a sectioned elevation view of an alternative embodiment of the APD cycler of the present disclosure performing an initial (or subsequent) patient drain.
Figure 11:
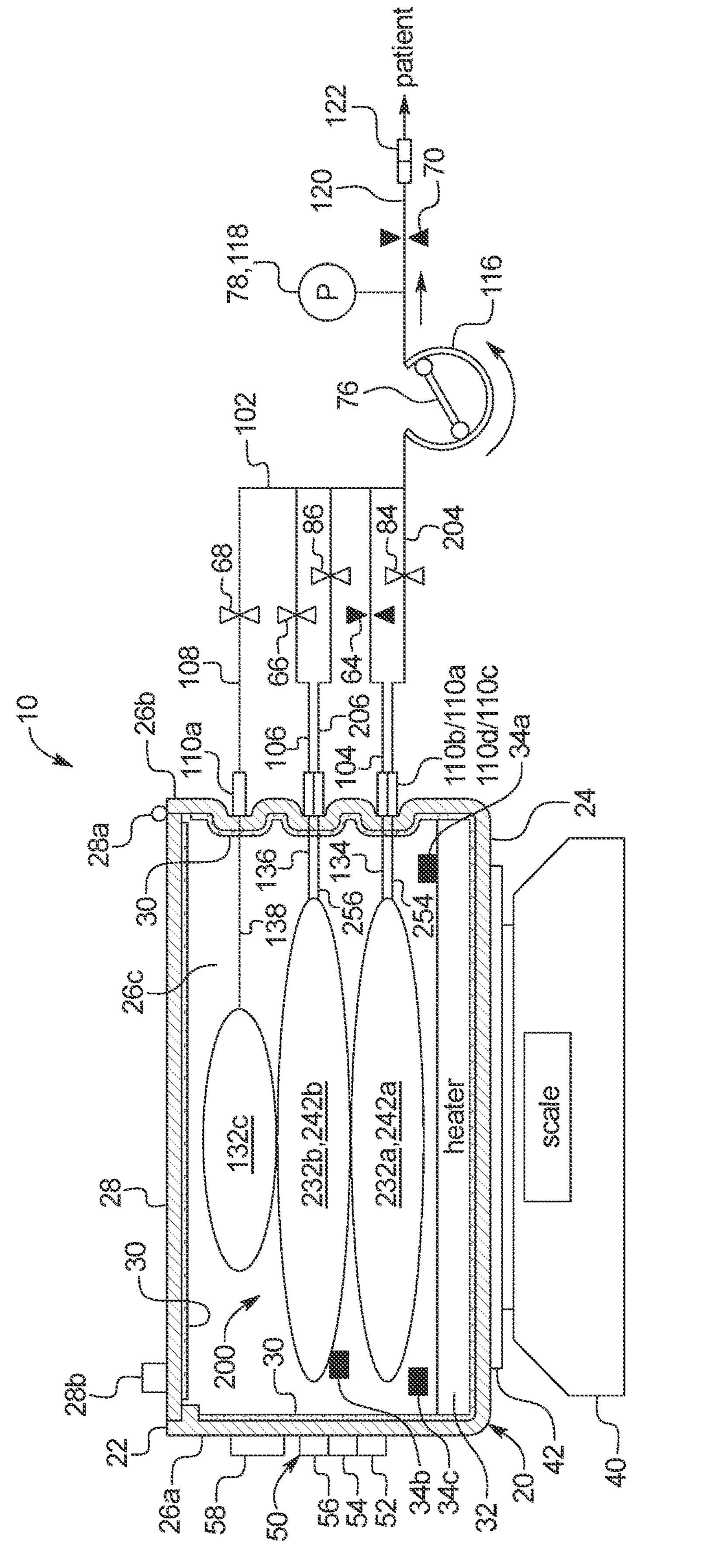
FIG. 11 is a sectioned elevation view of the alternative embodiment of the APD cycler in FIG. 10 performing a patient dwell.
Figure 12:
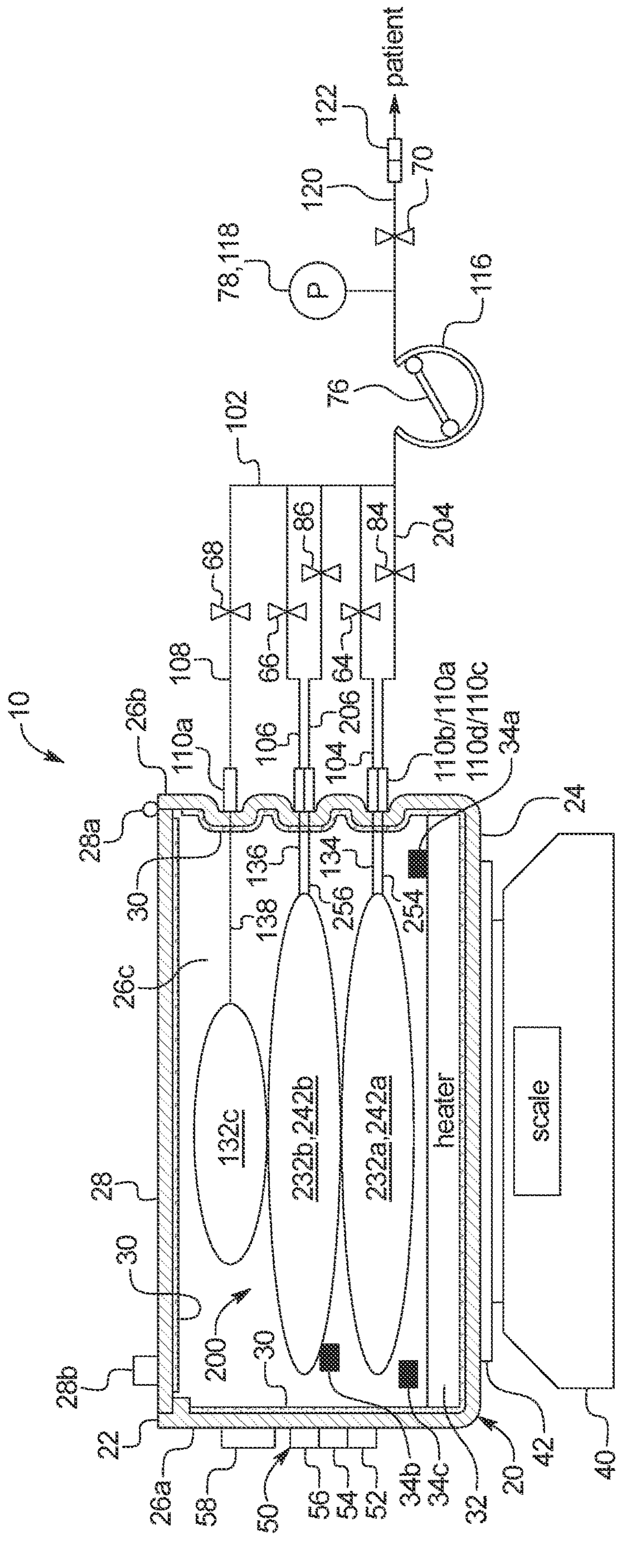
FIG. 12 is a sectioned elevation view of the alternative embodiment of the APD cycler in FIG. 10 performing a patient fill.

FIGS. 10 to 12 illustrate one embodiment for system 10 operating with alternative disposable set 200, wherein disposable set may use either PD fluid containers or bags 232*a*, 232*b* or 242*a*, 242*b*. In either case, last fill container 132*c* and associated container line 138 are also used. FIGS. 10 to 12 include many of the same components numbered the same as in FIGS. 3 to 5, which include all of the structure, functionality and alternatives discussed above in connection with FIGS. 3 to 5. The primary differences are that because drain container or bag 114 and drain line 112 are not provided, drain valve 62 is not provided. Also, terminal drain line 124 and corresponding drain valve 74 are not provided (but they may be for the reasons explained above). Drain valves 62 and 74 are replaced by (i) a first drain segment valve 84, under control of control unit 50, to open or occlude drain line segment 204 and (ii) a second drain segment valve 86, under control of control unit 50, to open or occlude drain line segment 206. Also, while FIG. 10 is illustrated as having multiple supply containers, a single supply container may be provided alternatively. For example, in FIGS. 10 to 12 a single supply container 232*a* or 242*a* may be provided alternatively along with last fill PD fluid container or bag 132*c*. Chamber 22 may be downsized accordingly.

FIGS. 10 to 12 illustrate used compartment lines 254 and 256 that extend from drain ports 240*b* or 246 of PD fluid containers or bags 232*a*, 232*b*, 242*a* or 242*b*. Used compartment lines 254 and 256 extend to drain container connectors 110*d*, which are configured to mate (e.g., in a color coded and/or keyed manner) with drain line connectors 110*c* discussed above in connection with FIG. 8. Supply line connectors 110*a* connect to supply container connectors 110*b* as illustrated and described above in connection with FIGS. 3 to 5.

FIG. 10 illustrates a situation at the beginning of treatment when the patient is full of effluent from a previous treatment (or from a manual fill in between treatments) and all three PD fluid containers or bags 232*a* or 242*a*, 232*b* or 242*b* and 132*c* are full of fresh fluid. At least the PD fluid in lower container 232*a* or 242*a* is heated to body temperature. An initial drain is performed in which used PD fluid from the previous treatment's last fill (or intervening manual fill), with valves 84 and 70 open (pinch arrows pulled apart in FIG. 10) and peristaltic pump actuator 76 operating in a clockwise direction, is pulled from the patient and pushed into the drain portion of PD fluid container or bag 232*a* or 242*a*. The initial (and any subsequent) patient drain stops in one embodiment when pressure transducer 78 senses a characteristic change (e.g., drop) in negative pressure, indicating that the patient is or is near empty (a feedback loop from transducer 78 to control unit 50 to pump actuator 76 may also be provided to reduce the pump speed when the pressure drops due to patient being near empty). The amount of the initial patient drain, including patient UF, is sensed by scale 40 and delivered to control unit 50. That amount may either be included in the present treatment's total UF calculation (total used fluid removed from the patient less total fresh fluid delivered to the patient) or may be included in the previous treatment's total UF calculation (total used fluid removed from the patient less total fresh fluid delivered to the patient), in which case the next treatment's initial drain is included in the present treatment's total UF calculation. The drain portion of first PD fluid container or bag 232*a* or 242*a* receives used dialysis fluid or effluent over multiple drains until the drain portion is full as measured by weigh scale 40. Afterwards, the drain portion of second PD fluid container or bag 232*b* or 242*b* receives used dialysis fluid or effluent over multiple drains. At the end of treatment. PD fluid containers or bags 232*a* or 242*a* and 232*b* or 242*b* are removed from chamber 22 and discarded. As before, terminal drain line 124 and corresponding drain valve 74 are not illustrated in FIG. 10 (but they may be for the reasons explained above).

It is quite possible that the patient is not full of used dialysis fluid or effluent at the beginning of treatment, which may occur if the patient does not receive a last fill at the end of treatment (e.g., last fill container 132*c* is not provided). In such a case, treatment begins with a patient fill. Again, control unit 50 may be configured to default to attempting a patient drain (safety drain) at the beginning of each treatment, which attempts to pull a small amount off effluent from the patient by applying a small negative pressure that does not cause the patient discomfort. When trying to pull the small amount of effluent, control unit 50 may (i) if a negative pressure increase is sensed, prompt the patient to check and see if a clamp that should be open is closed or if a patient or supply line is kinked, (ii) if all lines are clear after detecting the negative pressure increase, determine that the patient is dry and begin treatment with a patient fill, and (iii) if the negative pressure increase is not sensed, determine that the patient is full of effluent and begin treatment with a patient drain.

In any case, it is contemplated to prime disposable set 200 prior to the first patient fill. Here, control unit 50 causes each supply valve 64, 66 and 68 and patient line valve 70 to be opened and peristaltic pump actuator 76 to operate in a counterclockwise direction to pull fresh PD fluid from each of PD fluid containers 232*a* or 242*a*, 232*b* or 242*b* and 132*c*, which in turn drives air in lines 134/104, 136/106, 138/108 and 102 into patient line 120. In one priming example, control unit 50 causes supply valve 68 and patient valve 70 to open and peristaltic pump actuator 76 to slowly pull fluid from container 132*c*, so that fresh dialysis fluid reaches the inlet of the pump. Control unit 50 then causes supply valve 68 to close and first drain segment valve 84 to open and reverses peristaltic pump actuator 76 to push fresh dialysis fluid into used compartment line 254. Control unit 50 then causes supply valve 66 and patient valve 70 to open and peristaltic pump actuator 76 to slowly pull fluid from container 232*b*, 242*b*, so that fresh dialysis fluid again reaches the inlet of the pump. Control unit 50 then causes supply valve 66 to close and second drain segment valve 86 to open and reverses peristaltic pump actuator 76 to push fresh dialysis fluid into used compartment line 256. Control unit 50 then, assuming container 232*b*, 242*b* is used for the first fill, opens supply valve 64 and patient valve 70 to prime the whole set up to patient connector 122.

The amount of fresh PD fluid needed and delivered during priming may be known via corresponding tubing volume and controlled via a corresponding weight sensed by weigh scale 40. Priming patient line 120 up to patient connector 122 may be performed by pushing fresh PD fluid up to a hydrophobic membrane provided with patient connector 122, or to a prime sensor (e.g., optical, capacitive or other) outputting to control unit 50 and against which patient connector 122 at the distal end of patient line 120 is located prior to treatment.

FIG. 11 illustrates a patient fill for disposable set 200 in which control unit 50 causes supply valve 64 and patient valve 70 to be open (pinch arrows pulled apart in FIG. 11) and peristaltic pump actuator 76 operating in a counterclockwise direction to pull fresh dialysis fluid from the fresh fluid portion of PD fluid container 232*a* or 242*a* and to push same through patient line 120 to the patient. Assuming each fluid container 232*a* or 242*a* and 232*b* or 242*b* is heated to body temperature or 37° C., fresh PD fluid may be pulled from either container and from each container multiple times. If fluid containers 232*a* or 242*a* and 232*b* or 242*b* contain different glucose or dextrose level dialysis fluids, supply valves 64 and 66 may be sequenced to allow different PD fluids to be provided over different patient fills of a treatment, e.g., according to a prescribed patient prescription. Supply valves 64 and 66 may also be toggled via control unit 50 during a same patient fill to achieve an accurately weighed blend of PD fluid as may be called for by the patient's prescription. All patient fills of a treatment are completed and stopped in one embodiment when weigh scale 40 records a prescribed patient fill volume's worth of fresh PD fluid having left one or more of fluid containers 232*a* or 242*a*, 232*b* or 242*b* and 132*c*. Patient fill volumes may be the same or different for different patient fills of a treatment according to the patient's prescription. The fresh fluid portion of first PD fluid container or bag 232*a* or 242*a* may be used to supply fresh PD fluid over multiple patient fills of a treatment. Likewise, the fresh fluid portion of second PD fluid container or bag 232*b* or 242*b* may be used to supply fresh PD fluid over multiple patient fills of a treatment.

FIG. 12 illustrates one embodiment for a patient dwell for disposable set 200, which may again last on the order of one or more hour. During this time period, control unit 50 may perform one or a number of procedures to prepare for the next patient drain and patient fill. For example, control unit 50 may continue to heat a next PD fluid container 232*a* or 242*a*, 232*b* or 242*b* and 132*c*, so that it is ready as soon as the next patient drain is completed. Control unit 50 however does not have to remove used dialysis fluid to a terminal drain because the used dialysis fluid remains in fluid containers 232*a* or 242*a* and 232*b* or 242*b*.

The patient after treatment may wheel all of the used dialysis fluid to a house drain for removal, which is advantageous because less disposable material is used, saving cost and lessening environmental impact, and because a leaking house drain line is prevented. Each of the pumping procedures performed in connection with disposable set 200, except the priming procedure, involves either removing used dialysis fluid from or delivering fresh dialysis fluid to the patient. Control unit 50 receives output signals from pressure transducer 78 operating with pressure sensing pod 118 for each of the patient pumping procedures to use as feedback to control the speed of peristaltic pump actuator 76 so as to maintain any patient pumping within a safe pressure limit, e.g., within one to five psig for patient fills (e.g., two psig (14 kPa)) and −1.0 to −3.0 psig (e.g., 1.3 psig (−9 kPa)) for patient drains. Control unit 50 may alternatively be programmed to remove used dialysis fluid during treatment dwells or after treatment to drain using a dedicated drain line so that the patient does not have to transport containers full of effluent.

The sequence described above for FIGS. 10 to 12 is the same if containers 252*a* and 252*b* of FIG. 6B are used instead, except that a pair of lines and associated valves may be eliminated. For example, drain line segments 204 and 206 and connectors 110*c* may be removed along with associated valves 84 and 86. Used compartment lines 254 and 256 may also be eliminated. Supply lines 104, 106 remain and double as drain lines. Lines 104 and 106 are connected to ports 240*c* of containers 252*a* and 252*b*, respectively. Remaining valves 64 and 66 are opened under control of control unit 50 for both patient fills and patient drains.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, pneumatic valves, or other types of valves, may be used instead of electrically actuated pinch valves. Other types of pumping may also be used, such as diaphragm pumping and/or pneumatic pumping. In another example, inline heating may be used alternatively. In a further example, while the present disclosure illustrates the supply lines being matted via connectors 110*a* and 110*b* at a side, surface or wall of chamber 22, it is also contemplated to allow the supply lines of disposable set 100 to instead extend through a hole or slot in the side, surface or wall of chamber 22 and be connected directly to dialysis fluid containers or bags 132*a*, 132*b*, 132*c*, 232*a*, 232*b*, 242*a* and 242*b*. The same holds true for the drain lines associated with dialysis fluid containers or bags 232*a*, 232*b*, 242*a* and 242*b*. In a further example, while the pump and valve actuators are illustrated and described as being located outside of chamber 22, one or more or all of the pump and valve actuators may instead be located inside of the chamber. Also, while the pump and valve actuators are illustrated and described as being attached directly to chamber 22, one or more or all of the pump and valve actuators may instead be attached to a housing of the cycler supporting, providing or forming the chamber.

The invention is claimed as follows:

1. A peritoneal dialysis ("PD") system comprising:
a cycler including
a weigh scale,
a chamber positioned to be weighed by the weigh scale,
a heater supported by a bottom of the chamber configured to heat an inside of the chamber,
a plurality of valves supported by the chamber or a housing of the cycler,
at least one temperature sensor,
a pump supported by the chamber or a housing of the cycler, and
a control unit operable with the weigh scale, the heater, the plurality of valves and the pump; and
a disposable set including
a PD fluid container sized to fit within the chamber so as to be weighed by the weigh scale and heated by the heater,
a supply line in fluid communication with the PD fluid container and extending outside of the chamber,
a drain container sized to fit within the chamber so as to be weighed by the weigh scale,
a drain line in fluid communication with the drain container and extending outside of the chamber, and
a patient line positioned on an opposing side of the pump from the supply line and the drain line,
wherein the control unit is configured to operate the plurality of valves and the pump bidirectionally to pump (i) used dialysis fluid from the patient line, through the drain line, to the drain container and (ii) fresh dialysis fluid from the PD fluid container, through the supply line, and through the patient line,
wherein the control unit is further configured to receive output signals from the at least one temperature sensor and weight signals from the weigh scale and stop the pump when the weigh scale records a prescribed patient fill volume worth of the fresh dialysis fluid as having left the PD fluid container.

2. The PD system of claim 1, wherein the plurality of valves include a supply line valve, a drain line valve and a patient line valve, wherein the control unit is configured to open the drain line valve and the patient line valve for (i) of claim 1, and wherein the control unit is configured to open the supply line valve and the patient line valve for (ii) of claim 1.

3. The PD system of claim 2, wherein at least one of the supply line valve, drain line valve or patient line valve is a pinch valve that opens or occludes the supply line, drain line or patient line, respectively.

4. The PD system of claim 1, wherein the pump is a peristaltic pump, and wherein the disposable set includes a peristaltic pumping tube located between (a) the supply line and the patient line and (b) the drain line and the patient line.

5. The PD system of claim 1, wherein the PD fluid container is a first PD fluid container and the supply line is a first supply line, and which includes a second PD fluid container sized to fit within the chamber so as to be weighed by the weigh scale and heated by the heater, and a second supply line in fluid communication with the second PD fluid container and extending outside of the chamber.

6. The PD system of claim 5, wherein the chamber is configured for the second PD fluid container to be placed on top of the first PD fluid container.

7. The PD system of claim 5, wherein the chamber is configured for the second PD fluid container to be placed adjacent to the first PD fluid container.

8. The PD system of claim 5, wherein the patient line is positioned on the opposing side of the pump from the supply line, the drain line and the second supply line.

9. The PD system of claim 1, wherein the supply line mates with a container line extending from the PD fluid container.

10. The PD system of claim 9, wherein the mating of the supply line and the container line occurs along a side of the chamber supporting at least one of the supply line or the container line.

11. The PD system of claim 1, wherein the chamber is configured for the supply line to extend into the chamber for connection to the PD fluid container.

12. The PD system of claim 1, wherein the disposable set further includes a terminal drain line, and wherein the control unit is further configured to operate at least some of the plurality of valves and the pump to pump used dialysis fluid from the drain container, after the used dialysis fluid is weighed by the weigh scale, to the terminal drain line.

13. The PD system of claim 12, wherein the terminal drain line is positioned along with the patient line on the opposing side of the pump from the supply line and the drain line.

14. The PD system of claim 12, wherein the terminal drain line extends to a terminal drain container or to a house drain.

15. The peritoneal dialysis ("PD") system comprising:
- a cycler including
  - a weigh scale,
  - a chamber positioned to be weighed by the weigh scale,
  - a heater supported by a bottom of the chamber configured to heat an inside of the chamber,
  - a plurality of valves supported by the chamber or a housing of the cycler,
  - at least one temperature sensor,
  - a pump supported by the chamber or a housing of the cycler, and
  - a control unit operable with the weigh scale, the heater, the plurality of valves and the pump; and
- a disposable set including
  - a PD fluid container sized to fit within the chamber so as to be weighed by the weigh scale and heated by the heater, the PD fluid container including a fresh PD fluid compartment and a used PD fluid compartment,
  - a supply line in fluid communication with the fresh PD fluid compartment and extending outside of the chamber,
  - a drain line in fluid communication with the used PD fluid compartment and extending outside of the chamber, and
  - a patient line positioned on an opposing side of the pump from the supply line and the drain line,
- wherein the control unit is configured to operate the plurality of valves and the pump bidirectionally to pump (i) used dialysis fluid from the patient line, through the drain line, to the used PD fluid compartment and (ii) fresh dialysis fluid from the fresh PD fluid compartment, through the supply line, and through the patient line,
- wherein the control unit is further configured to receive output signals from the at least one temperature sensor and weight signals from the weigh scale and stop the pump when the weigh scale records a prescribed patient fill volume worth of the fresh dialysis fluid as having left the PD fluid container.

16. The PD system of claim 15, wherein (i) the supply line mates with a fresh compartment line extending from the fresh PD fluid compartment and (ii) the drain line mates with a used compartment line extending from the used PD fluid compartment.

17. The PD system of claim 15, wherein the chamber is configured for (i) the supply line to extend into the chamber for connection to the fresh PD fluid compartment and (ii) the drain line to extend into the chamber for connection to the used PD fluid compartment.

18. The PD system of claim 15, wherein the chamber is sized to hold an entire fresh PD fluid volume at a beginning of a treatment and used PD fluid from multiple drains at the end of the treatment.

19. A peritoneal dialysis ("PD") system comprising:
- a cycler including
  - a weigh scale,
  - a chamber positioned to be weighed by the weigh scale,
  - a heater supported by a bottom of the chamber configured to heat an inside of the chamber,
  - a plurality of valves supported by the chamber or a housing of the cycler,
  - at least one temperature sensor,
  - a pump supported by the chamber or a housing of the cycler, and
  - a control unit operable with the weigh scale, the heater, the plurality of valves and the pump; and
- a disposable set including
  - a PD fluid container sized to fit within the chamber so as to be weighed by the weigh scale and heated by the heater, the PD fluid container including a fresh PD fluid compartment and a used PD fluid compartment, a first one-way valve in fluid communication with the fresh PD fluid compartment, the first one-way valve oriented to open under negative pressure from outside the fresh PD fluid compartment, a second one-way valve in fluid communication with the used PD fluid compartment, the second one-way valve oriented to open under positive pressure from outside the used PD fluid compartment,
  - a supply/drain line in fluid communication with the first and second one-way valves, the supply/drain line extending outside of the chamber, and
  - a patient line positioned on an opposing side of the pump from the supply/drain line,
- wherein the control unit is configured to operate the plurality of valves and the pump bidirectionally to pump (i) used dialysis fluid from the patient line, through the supply/drain line and the second one-way valve, to the used PD fluid compartment and (ii) fresh dialysis fluid from the fresh PD fluid compartment, through the first one-way valve and the supply/drain line, through the patient line,
- wherein the control unit is further configured to receive output signals from the at least one temperature sensor and weight signals from the weigh scale and stop the pump when the weigh scale records a prescribed patient fill volume worth of the fresh dialysis fluid as having left the PD fluid container.

20. The PD system of claim 19, wherein the supply/drain line mates with a tee extending to a first port holding the first one-way valve and a second port holding the second one-way valve.

21. The PD system of claim 19, wherein the chamber is sized to hold an entire fresh PD fluid volume at a beginning of a treatment and used PD fluid from multiple drains at the end of the treatment.

22. A peritoneal dialysis ("PD") system comprising:
- a cycler including
  - a weigh scale,
  - a chamber positioned to be weighed by the weigh scale,
  - a heater supported by a bottom of the chamber configured to heat an inside of the chamber, a plurality of valves supported by the chamber or a housing of the cycler, at least one temperature sensor, a pump supported by the chamber or a housing of the cycler, and a control unit operable with the weigh scale, the heater, the plurality of valves and the pump; and a disposable set including a PD fluid container sized to fit within the chamber so as to be weighed by the weigh scale and heated by the heater, the PD fluid container including a fresh PD fluid end and a used PD fluid end, a supply line in fluid communication with the fresh PD fluid end and extending outside of the chamber, a drain line in fluid communication with the used PD fluid end and extending outside of the chamber, and a patient line positioned on an opposing side of the pump from the supply line and the drain line, wherein the control unit is configured to operate the plurality of valves and the pump bidirectionally to pump (i) used dialysis fluid from the patient line, through the drain line, to the used PD fluid end of the PD fluid container and (ii) fresh dialysis fluid from the fresh PD fluid end of the PD fluid container, through the supply line, and through the patient line, wherein the control unit is further configured to receive output signals from the at least one temperature sensor and weight signals from the weigh scale and stop the pump when the weigh scale records a prescribed patient fill volume worth of the fresh dialysis fluid as having left the PD fluid container.

23. The PD system of claim 22, wherein (i) the supply line mates with a fresh compartment line extending from the fresh PD fluid end of the PD fluid container and (ii) the drain line mates with a used compartment line extending from the used PD fluid end of the PD fluid container.

24. The PD system of claim 22, wherein the chamber is configured for the (i) supply line to extend into the chamber for connection to the fresh PD fluid end of the PD fluid container and (ii) the drain line to extends into the chamber for connection to the used PD fluid end of the PD fluid container.

25. The PD system of claim 22, wherein the used PD fluid end of the PD fluid container includes a drain inlet barrier for dampening incoming used PD fluid flow.

26. The PD system of claim 22, wherein fresh PD fluid and used PD fluid within the PD fluid container meet at a fresh/used PD fluid interface.

* * * * *